US008535319B2

(12) United States Patent
Ball

(10) Patent No.: US 8,535,319 B2
(45) Date of Patent: Sep. 17, 2013

(54) SURGICAL GUIDE SYSTEMS AND METHODS FOR PROSTHETIC JOINTS

(75) Inventor: Robert J. Ball, West Olive, MI (US)

(73) Assignee: Tornier, Montbonnot Saint Martin (FR)

(*) Notice: Subject to any disclaimer, the term of this patent is extended or adjusted under 35 U.S.C. 154(b) by 261 days.

(21) Appl. No.: 12/954,423

(22) Filed: Nov. 24, 2010

(65) Prior Publication Data

US 2011/0130795 A1     Jun. 2, 2011

Related U.S. Application Data

(60) Provisional application No. 61/263,985, filed on Nov. 24, 2009.

(30) Foreign Application Priority Data

Jan. 15, 2010   (FR) ...................................... 1050267

(51) Int. Cl.
*A61B 17/56* (2006.01)

(52) U.S. Cl.
USPC .......................................... 606/86 R; 606/96

(58) Field of Classification Search
USPC ............ 606/86 R, 96, 130; 623/19.11, 19.13
See application file for complete search history.

(56) References Cited

U.S. PATENT DOCUMENTS

| 5,030,219 A | 7/1991 | Matsen, III et al. |
| 7,175,663 B1 * | 2/2007 | Stone .......................... 623/19.13 |
| 2002/0077540 A1 * | 6/2002 | Kienzle, III ................... 600/424 |
| 2004/0230197 A1 | 11/2004 | Tornier et al. |
| 2009/0226068 A1 | 9/2009 | Fitz et al. |

FOREIGN PATENT DOCUMENTS

| EP | 0903127 A2 | 3/1999 |
| EP | 1457159 A1 | 9/2004 |

OTHER PUBLICATIONS

European Search Report issued in EP Application No. 10191950, dated Mar. 9, 2011, 4 pages.
France Search Report issued in FR Application No. 1050267, dated Aug. 12, 2010, 2 pages.

* cited by examiner

*Primary Examiner* — Kevin T Truong
*Assistant Examiner* — Christian Sevilla
(74) *Attorney, Agent, or Firm* — Faegre Baker Daniels LLP

(57) ABSTRACT

A surgical system for assisting in the implanting of a glenoid component of a shoulder prosthesis in a patient includes a guide having guide features for guiding application of the bone preparation tool to the glenoid and a series of graphic representations of the glenoid component shown being implanted on the glenoid with different implant positions, each of which is associated with one of the graphic representations.

21 Claims, 3 Drawing Sheets

SURGICAL GUIDE SYSTEMS AND METHODS FOR PROSTHETIC JOINTS

CROSS-REFERENCE TO RELATED APPLICATION

This application claims priority to U.S. Provisional Application No. 61/263,985, filed Nov. 24, 2009 and French Application No. FR 10 50267, filed Jan. 15, 2010, both of which are herein incorporated by reference in their entireties.

TECHNICAL FIELD

The present invention relates to a surgical assembly for assisting in the implanting of a glenoid component of a shoulder prosthesis on a patient.

BACKGROUND

Replacing the glenoid articular surface of the scapula of a human being with a glenoid prosthetic component of a shoulder prosthesis is a delicate surgical operation. It has been found that, depending on the position of implantation of this glenoid component, risks of separation of the component exist, because of the modification of forces applied to this component in subsequent movements of the prosthetic shoulder. Currently, orthopedic surgeons choose such a glenoid component from a range of implants, having geometries, notably sizes, that are slightly different from one another. Then they empirically estimate the position of the implantation of the selected glenoid component, notably by visually assessing the geometry of the glenoid surface of the patient to be operated on. The surgeon tries peroperatively, to choose and implant the prosthetic component on the scapula so that, when in service, this component reproduces the kinematics of the patient's original glenoid articular surface, while being firmly and stably fixed to the socket.

Another approach includes utilizing preoperative mapping data relating to the socket of the patient to fabricate a custom glenoid component, where a custom component would be specifically customized to the particular patient being operated upon. The customization of the component facilitates attachment of the component to the glenoid, also described as a socket, by taking account of the precise characteristics of the glenoid, which are specific to the patient being operated upon. This kind of customized solution can be very costly.

SUMMARY

Some embodiments of the present invention provide a surgeon simple means for assisting in optimizing the position of implantation of a "standard" glenoid component—a glenoid component that is not necessarily customized for the glenoid of a particular patient. While various embodiments are described in association with procedures and components for repairing the shoulder joint, and in particular the glenoid, embodiments relating to other joints are also contemplated, including the hip joint, and in particular the acetabulum, for example.

With the foregoing in mind, various embodiments provide a surgical approach with an efficient means for carrying out, for each patient operated upon, a customized implantation of a socket component of a prosthetic joint, such as a glenoid component.

Some embodiments relate to a surgical assembly for assisting in the implanting of a glenoid component of a shoulder prosthesis in a patient. The assembly includes a guide for preparing the glenoid of the patient, the guide including a plate configured to be pressed into a complementary fit with the glenoid of the patient. The plate includes guide means for providing several tool positions for a socket preparation tool. For example, the guide means optionally include several fixed guide features for guiding use of a socket preparation tool on the glenoid. In some embodiments, the guide features include stationary holes in the plate that provide a plurality of different tool positions that can be used to guide use of a socket drill bit, or other tool. The guide features additionally or alternatively include one or more adjustable components for guiding the socket preparation tool (e.g., guide features that are configured to be displaced—such as by relative rotation or sliding—to select between different tool positions).

Some embodiments relate to methods of surgical intervention with a preparation tool, such as preparing the glenoid of the patient for receiving a glenoid component of a joint prosthesis. The method includes selecting a tool position on the guide for the preparation tool and applying the preparation tool using the selected tool position. In some embodiments, the surgeon's tool position selection is made according to a graphic representation of the socket of the patient and a glenoid component shown being hypothetically implanted on this socket according to the particular tool position that is to be utilized to prepare the glenoid. In some embodiments, the graphic representations are as numerous as there are different tool positions provided by the guide features. In other words, the graphic representations are optionally as numerous as the tool position options provided by the fixed guide features and/or adjustable guide features of a mobile guidance member—each graphic representation being associated with a corresponding tool position on a one-to-one basis according to a predictive relationship.

In some embodiments, by using the graphic representation associated with a first tool position associated with a fixed guide feature or an adjustable guide feature, the surgeon can directly and easily view a position (e.g., angular orientation) in which the glenoid component of the patient will be implanted, assuming that the surgeon would guide the application of the preparation tool using that first tool position provided by the fixed or adjustable guide feature. Similarly, by virtue of the graphic representation associated with a second tool position provided by a fixed or adjustable guide feature, the surgeon views the position (e.g., angular orientation) in which the glenoid component would be implanted on the socket assuming that the surgeon would guide the preparation tool according to the second tool position provided by the second guidance feature, and so forth for other graphic representations and tool positions. In practice, the various graphic representations and the corresponding tool positions are provided to select the relative position of implantation between the socket and the glenoid component according to one or more degrees of freedom which the surgeon is advantageously used to adjusting to facilitate implantation of the glenoid component.

In other words, the plurality of graphic representations, respectively associated with the different degree(s) of freedom envisaged for the implantation, provide the surgeon with the different possibilities for the implantation of the glenoid component on the specific glenoid of the patient who will be operated on, depending on whether the surgeon uses a particular tool position according to a fixed and/or adjustable guide feature to form or otherwise prepare the glenoid for the glenoid component with a preparation tool. Visually, the surgeon assesses (preoperatively, in some embodiments) the medical situation specific to the patient undergoing the procedure and decides on the optimal implantation configuration based upon patient anatomy, available glenoid components, and/or other factors. Thus, according to some embodiments, by virtue of the identification of the graphic representation, the surgeon is provided with an indication which fixed guide feature and/or to which position to move an adjustable guide feature preoperatively to guide application of the socket bone preparation tool in order to effectively carry out fitting of the glenoid component.

In some embodiments, the tool position to be used in preparing the socket is selected preoperatively using the graphic representations, where the available tool positions and corresponding graphic representations are based upon preoperational mapping data relating to the socket of the particular patient to be operated on, as well as preestablished dimensional data relating to the glenoid component(s) to be implanted, as well as other factors as appropriate. Furthermore, by virtue of these graphic representations, the surgeon can easily adjust an intervention strategy, and if necessary, just before the intervention.

In some embodiments, a method for determining the graphic representations to be provided on a guide includes using preestablished dimensional data relating to the glenoid component and preoperational mapping data relating to the glenoid of the patient to determine a plurality of different, hypothetical positions of implantation of a glenoid component by calculation. In some embodiments, the hypothetical positions are distributed according to a degree of freedom predefined for the plurality of hypothetical positions of implantation. For each of the determined implantation positions, a graphic representation is provided that corresponds to the glenoid of the patient and the glenoid component hypothetically implanted on the glenoid. A user of the guide presses the guide onto the glenoid of the patient and selects one of the graphic representations provided on the guide. A fixed and/or adjustable guide feature corresponding to the graphic representation is then utilized to guide application of a bone preparation tool to the glenoid. The glenoid is prepared and the glenoid component is fitted on the socket prepared by the tool.

Some embodiments relate to a surgical system for assisting in the implanting of a glenoid component of a shoulder prosthesis in a patient. The system includes a guide for guiding application of a bone preparation tool to a glenoid, the guide having a bearing face configured to be fitted to the glenoid and guide features for guiding application of the bone preparation tool to the glenoid. The system also includes a series of graphic representations of the glenoid component hypothetically implanted on the glenoid with different implant positions, the respective implant positions of implantation of the glenoid component varying according to a degree of freedom, the guide features being configured to guide the application of the bone preparation tool to the glenoid according to a series of tool positions, each of which is associated with one of the implant positions.

Some embodiments relate to a method of preparing a glenoid of a patient for receiving a glenoid component of a joint prosthesis. The method includes fitting a guide to a glenoid of a patient, the guide having a bearing face fitted to the glenoid and guide features for guiding application of a bone preparation tool to the glenoid. The method also includes selecting a guide feature for guiding application of the preparation tool based upon a plurality of graphic representations of the glenoid component hypothetically implanted on the glenoid with different implant positions, the guide features of the guide being associated with one of the graphic representations and applying the preparation tool using the selected tool position.

Still other embodiments relate to a method of providing a surgical system for assisting in the implanting of a glenoid component of a shoulder prosthesis in a patient, the method including generating a plurality of graphic representations of a plurality of implant positions of the glenoid component hypothetically implanted in the glenoid of the patient based upon preoperational mapping data relating to the glenoid of the patient and preestablished dimensional data relating to the glenoid component to be implanted. The method also includes providing a guide for guiding application of a bone preparation tool to the glenoid to prepare the glenoid for receiving the glenoid component at a different one of the implant positions, the guide having a bearing face configured to be fitted to the glenoid and guide features for guiding application of the bone preparation tool, each of the guide features being configured to prepare the glenoid for receiving the glenoid component according to one of the implant positions.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

As previously noted, the drawings are to be regarded as illustrative in nature and not restrictive.

DETAILED DESCRIPTION

Figure 1:
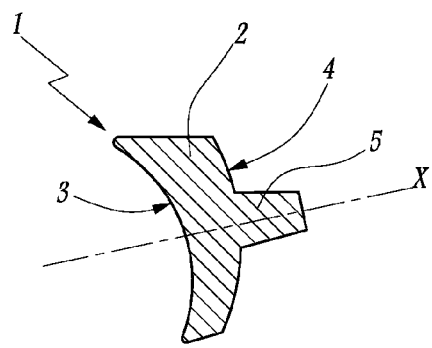
FIGS. 1 and 2 are schematic cross sections in a frontal plane of a patient to be operated on, FIG. 1 showing a glenoid component to be implanted whereas that of FIG. 2 shows the socket of the patient to be prosthetized, according to some embodiments.

FIG. 1 shows a glenoid component 1 of a shoulder prosthesis, which includes an implant body 2 having a cup-shape. As shown, the implant body 2 delimits two opposite main faces, namely an articular face 3 that is concave and a bearing face 4 that is convex. More specifically, the articular face 3 is configured, at least partly, to be articulated against a substantially complementary surface, not represented in the figures, delimited either by the anatomical upper end of a humerus, or by a humeral component of the abovementioned shoulder prosthesis, for example. In the example shown in FIG. 1, this articular face 3 is concave but, in other embodiments the articular face 3 is convex (not shown), the corresponding shoulder prosthesis then being generally described as an inverted prosthesis. As shown, the bearing face 4 is configured to be pressed, directly or indirectly, against the lateral bone end of a scapula. In other words, the bearing face 4 is configured, or is otherwise shaped and sized, to be engaged with a glenoid G (FIG. 2), or socket, of the scapula. In some embodiments, the glenoid G is prepared for this purpose. As shown, the bearing face 4 is provided with bone anchoring means in the socket in the form of a protruding keel 5, also described as a fin or wedge, although other anchoring means (e.g., prongs, projections, and/or other anchoring features) are contemplated.

The glenoid component 1 of FIG. 1 is an illustrative example, shown schematically. The present invention applies to glenoid components produced in widely varying forms. For example, the implant body 2 is optionally of a single piece or of an assembly of several parts, with one or more materials, either metallic or plastic, ceramic or pyrocarbon, forming the implant body 2. As another example, bone anchoring means other than the keel 5 are contemplated, where preparation of the glenoid on which the glenoid component 1 is to be installed is adapted to receive the particular bone anchoring means.

Figure 2:
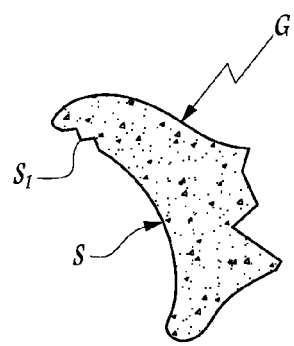

FIG. 2 shows the glenoid G of the scapula of a patient. The glenoid G is shown in its anatomical configuration, where the glenoid G delimits a glenoid surface S which is essentially concave, and against which the anatomical head of the patient's humerus (not shown) normally articulates. In some embodiments, the glenoid G of the patient is fitted with a prosthetic glenoid component, or is prosthesized, for pathological or accident reasons.

Figure 3:
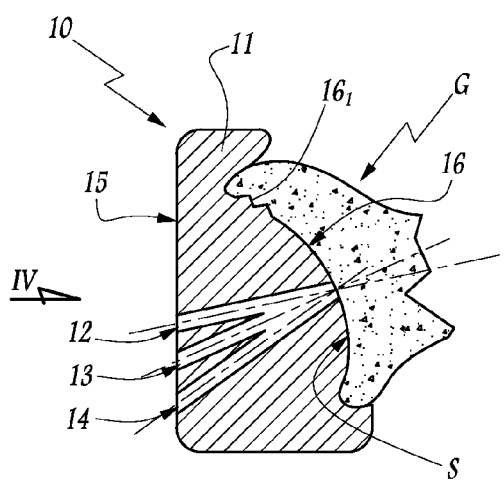
FIG. 3 is a view similar to FIG. 2, showing the use of a guide having fixed guide features and belonging to surgical system, according to some embodiments.
Figure 4:
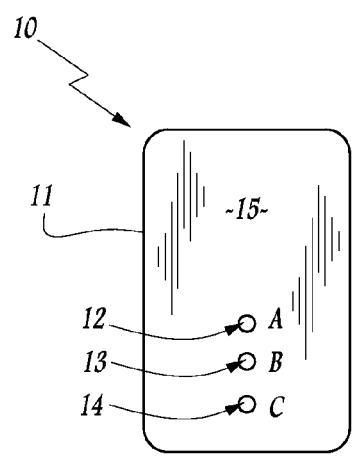
FIG. 4 is an elevation view according to the arrow IV of FIG. 3, according to some embodiments.
Figure 5:
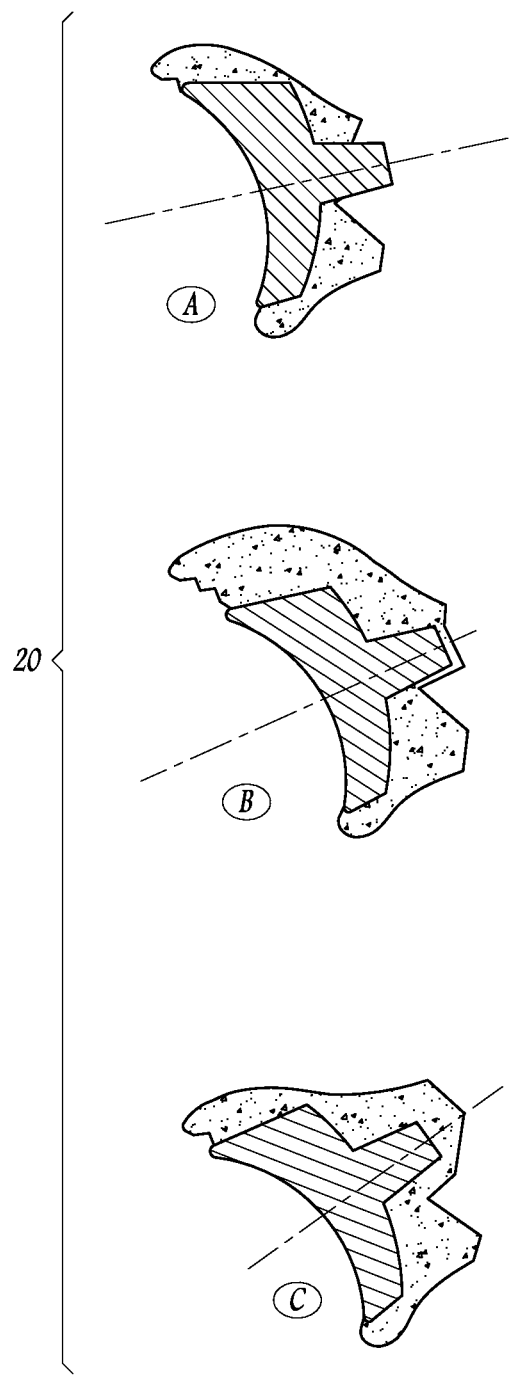
FIG. 5 is a diagram showing a plurality of graphic representations, belonging to the surgical assembly, according to some embodiments.

In some embodiments, the glenoid component 1 of FIG. 1 is implanted on the glenoid G of FIG. 2 during a surgical intervention in an "optimum" or preferential implantation configuration by a surgeon, where the surgeon adjusts a position of the glenoid component 1 on the glenoid G in one or more degrees of freedom. FIGS. 3 to 5 generally show means for adjustment of the inclination of the glenoid component 1 relative to the glenoid G in the frontal plane of the patient, which corresponds to the cross-sectional plane of FIGS. 1 and 2, although adjustment in other degrees of freedom (e.g., the anterior-posterior direction) are also contemplated.

FIGS. 3 to 5 show a guide 10 that provides means for selecting or otherwise adjusting the inclination of the glenoid component 1, in the abovementioned plane, of the longitudinal main axis X of the keel 5. The inclination, or position, of the glenoid component 1 with respect to the glenoid G is determined by forming a channel for accommodating the keel 5 having a corresponding inclination, where a surgeon or other user hollows out the channel in the glenoid G using a preparation tool (e.g., the bit of a drill, not shown) in conjunction with the guide 10.

The guide 10 includes a plate 11 which has a plurality of guide features in the form of three distinct holes 12, 13 and 14 that pass from one side to the other side, through the plate 11. The holes 12, 13, 14 are each configured to guide the abovementioned drill bit at a corresponding tool position, the transversal cross-section of each of these holes 12, 13, 14 being complementary in shape to the transversal cross-section of the bit. The holes 12, 13 and 14 thus link two opposite faces of the plate 11, namely a proximal face 15, which, in service, is turned towards the surgeon, and a distal face 16 which is configured to fit snugly to the glenoid surface S of the glenoid G of the patient and which, in service, is pressed against the glenoid G.

In some embodiments, the central axes of the holes 12, 13 and 14 belong to one and the same plane which, when the plate 11 is pressed onto the glenoid G, corresponds to the frontal plane of the patient, which is also the cross-sectional plane along which the views of FIGS. 1 and 2 are taken. Furthermore, the axes of these holes converge, or are substantially concurrent, at a point on distal face 16. In other words, the axes of the holes 12, 13, 14 converge toward one another at a location moving away from the proximal face 15 until they open out on the distal face 16 in the form of a common orifice in the distal face 16. In use, depending on the hole used out of the holes 12, 13 and 14 to guide the abovementioned drill bit, the channel formed in the glenoid will be more or less inclined in the frontal plane of the patient.

As shown in FIG. 4, the holes 12, 13 and 14 are visually identified on the proximal face 15 of the guide 10 by indicia. In the example shown in FIG. 4, the ends of the holes 12, 13 and 14 on the face 15 are identified by letters, namely, respectively "A," "B," and "C," inscribed on the face 15. As shown in FIG. 5, each of the letters corresponds to one of a plurality of graphic representations, or drawings, showing the glenoid G of the patient operated on and the glenoid component 1 hypothetically implanted on this glenoid at a particular orientation, or position. The glenoid G and the glenoid component 1 are drawn in the graphic representations in the frontal plane of the patient corresponding to the cross-sectional plane of FIGS. 1 and 2, though other sectional planes are contemplated. The three graphic representations of the plurality of graphic representations 20 are distinguished from one another based upon the glenoid component 1 being hypothetically implanted on the glenoid G in three different positions. As shown in FIG. 5, the three positions of implantation differ by the inclination of the axis X in the abovementioned frontal plane.

In some embodiments, a predictive relationship is provided between the plurality of graphic representations 20 and the guide 10. In practice, the implantation inclination shown by the topmost graphic representation in FIG. 5 is achieved by the surgeon if the surgeon uses the hole 12 to hollow out the channel for receiving the keel 5—the predictive relationship between use of the hole 12 and a particular orientation for the glenoid component 1 is indicated by identification of the hole 12 by the letter "A" on the proximal face 15 and identification on the first of the plurality of graphic representations 20 with the letter "A." Similarly, the bottommost graphic representation of the plurality of graphic representations 20 in FIG. 5 shows the implantation inclination of the glenoid component 1 on the glenoid G assuming that it is the guidance hole 14 that is used, which explains why this graphic representation is identified by the letter "C" used to identify the hole 14. A similar predictive relationship exists between the guidance hole 13 and the intermediate graphic representation between the graphic representations "A" and "C", hence the use of the identification letter "B".

To help better understand the predictive relationship mentioned hereinabove, there now follows a description of how the guide 10 and the plurality of graphic representations 20 are obtained then used in order to implant the glenoid component 1 on the glenoid G of the patient, according to various embodiments.

In some embodiments, prior to the actual surgical implantation intervention, mapping data is collected relating to the glenoid G of the patient to be operated on. In practice, these preoperational mapping data can be obtained in various ways. As an example, scanner images of the glenoid G are used: in particular, in the exemplary implementation considered here, at least one scanner image of the glenoid G is produced in the frontal plane corresponding to the cross-sectional plane of FIG. 2.

Moreover, in some embodiments, dimensional data relating to the glenoid component 1 is available preoperatively. In practice, these dimensional data are generally made available by the manufacturer of the glenoid component 1. In the absence of such data, or as otherwise desired, the dimensional data is obtained by appropriate measurements.

In some embodiments, and still preoperatively, the preoperational mapping data relating to the glenoid G, and the preestablished dimensional data relating to the glenoid component 1 are used to determine, by calculation, several hypothetical positions of implantation, by adjusting at least one predefined degree of freedom. In the case of the implementation considered in respect to the FIGS. 1-5, the degree of freedom corresponds to a change in inclination. For example, the three positions of inclination shown by the graphic representations of the plurality of graphic representations 20 are optionally determined based upon the preestablished dimensional data and preoperational data as described above. In practice, it may be advantageous to adjust the implantation inclination by distributing, in a predetermined manner, the various hypothetical positions of implantation over a desired range. For example, in some embodiments, the inclination of the axis X varies with a pitch of one degree between the different graphic representations.

Advantageously, it will be noted that the method, described hereinabove, for obtaining the plurality of graphic representations 20 (e.g., based upon preoperational mapping data relating to the glenoid G and the preestablished dimensional data relating to the glenoid component 1) may be implemented by an operator who has little or even no medical knowledge.

In some embodiments, the guide 10 is fabricated so that the guidance holes 12, 13, 14 correlate on a one-to-one basis with the three graphic representations 20. For this, the holes 12, 13 and 14 are designed, when the plate 11 is pressed on the glenoid surface S of the glenoid G, to apply a drill bit according to three different configurations, more specifically to guide this bit in respective directions which correspond to the inclinations of the three graphic representations 20. As explained above, these guidance holes 12, 13 and 14 are respectively associated on a one-to-one basis with the graphic representations indentified by the letters "A", "B" and "C".

In some embodiments, the predictive correlation between the holes 12, 13 and 14 and the three graphic representations 20 involves a predetermined accurate positioning of the plate 11 on the glenoid G during the use of the guide 10. A snug conformation of the distal face 16 with respect to the glenoid surface S of the glenoid G contributes to accurate positioning of the plate 11 on the glenoid G. In some embodiments, the close conformance and fit between the plate 11 and the glenoid G is exclusively utilized to ensure accurate positioning of the plate 11. In some embodiments, the distal face 16 of the plate 11 is specifically customized to the patient so as to allow only a single mechanical cooperation configuration, or fit, between the plate 11 and the glenoid G. For example, a rigorous adaptation of the face 16 with respect to the glenoid surface S is optionally provided by using the preoperational mapping data relating to the glenoid G during fabrication of the plate 11, where the distal face 16 of the plate 11 has reliefs that are specifically customized to the patient operated on. For example, as shown in FIG. 3, the reliefs $16_1$ are adjusted strictly to a damaged region $S_1$ situated in the top portion of the glenoid surface S.

Other solutions can be envisaged for accurately identifying the positioning of the plate 11 on the glenoid G when using the guide 10. For example, mechanical graduated systems or optical, ultrasonic and/or electromagnetic identification systems are additionally or alternatively utilized to select a position for the plate 11 on the glenoid G.

In some embodiments, during the surgical implantation intervention, the surgeon visually reviews the plurality of graphic representations 20. In practice, for this purpose, the plurality of graphic representations 20 are supplied to the surgeon on a printed medium, for example on sheets of paper, or are displayed for the surgeon on video screens. The surgeon has the discretion to choose, from the plurality of graphic representations 20, the graphic representation that the surgeon estimates to be most appropriate for the patient being operated on. The surgeon then finds the letter identifying this graphic representation among the letters "A", "B" and "C" on the guide 10. In some embodiments, the surgical intervention continues and, after having incised the soft parts surrounding the shoulder of the patient, the surgeon presses the distal face 16 of the plate 11 of the guide 10 onto the glenoid surface S of the glenoid G of the patient, until the plate 11 is appropriately positioned against the glenoid G. The surgeon then hollows out the glenoid G using a drill bit guided by the selected one of the holes 12, 13 and 14 that is associated with the graphic representation that the surgeon previously chose from the plurality of graphic representations 20. In practice, the surgeon identifies the relevant hole by virtue of the identification letter corresponding to the abovementioned graphic representation. While letters (e.g., "A," "B," and "C") are indicated as the indicia on the guide 10, it should be understood that other indicia (e.g., symbols or even the graphic representations themselves) are placed on the guide 10 for indicating to the surgeon which graphic representation corresponds to which guide feature and corresponding tool position.

The surgical intervention is completed with the fitting of the glenoid component 1 on the glenoid G, by introducing its keel 5 into the channel that the surgeon has just hollowed out in the glenoid G using the preparation tool.

Figure 6:
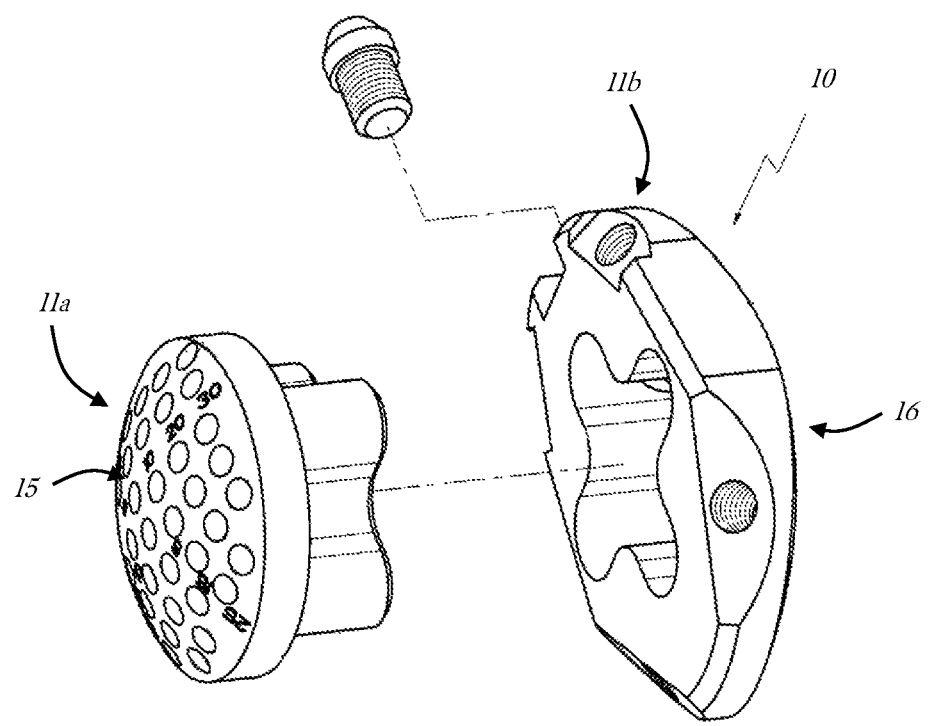
FIG. 6 shows another guide having mobile guide features, according to some embodiments.

FIG. 6 shows another guide 10 having mobile guide features, according to some embodiments. As shown, the guide 10 includes a plate 11 having a first portion 11a and a second portion 11b, the first portion having a plurality of guide features in the form of distinct holes that pass from one side to the other side, through the first portion 11a. The holes are each configured to guide the abovementioned drill bit at a corresponding tool position, the transversal cross-section of each of these holes being complementary in shape to the transversal cross-section of the bit. The first portion 11a defines a proximal face 15 of the guide 10 and the second portion 11b defines a distal face 16 of the guide 10, where the distal face is configured to fit snugly to the glenoid surface S of the glenoid G of the patient and which, in service, is pressed against the glenoid G. The first and second portions 11a, 11b are adapted to be rotated relative to one another and thereby adjusted through a plurality of pre-selected positions such that the guide features defined by the holes are mobile, or moveable to a desired configuration corresponding to a desired tool position. In some embodiments, the plurality of graphical representations 20 includes an implant position for each of the guide features, at each of the pre-selected positions.

Various arrangements and variants of the guide 10, of the plurality of graphic representations 20 and of the implantation method are also contemplated. By way of examples:

at least one other degree of freedom, other than the inclination in a frontal plane of the patient, for example, is utilized for the positions of implantation shown by the plurality of graphic representations 20, both individually and in combination with one another; such is, for example, the case for the anteroposterior deflection of the glenoid component 1 relative to the glenoid G in a plane transversal to the patient, for the positioning height-wise in the frontal plane, and for the glenoid version angle. Where several degrees of freedom are to be taken into consideration, the graphic representations of the positions of implantation according to the various degrees of freedom are optionally shown as a matrix of graphic representations;

as mentioned above, the anchoring of the glenoid component 1 of the glenoid G is accomplished by means other than the keel 5 that involve different bone preparation technique(s) for the glenoid through the use of tools that may differ from a drill bit, such as pins or saw blades, with corresponding guide features of these other tools being provided with the guide (e.g., guide features other than the guide holes 12, 13 and 14, such as non-cylindrical holes or cutting slots);

rather than providing fixed guided features on the plate 11, such as the holes 12, 13, 14, mobile guide features are optionally added to the plate via a mobile guide member, such as the guide described in U.S. application Ser. No. 10/793,947, entitled "ANCILLARY TOOL FOR POSITIONING A GLENOID IMPLANT," the entire contents of which are incorporated herein by reference for all purposes; the mobile guide member is optionally selectively adjusted (e.g., rotated) relative to the plate 11 between a succession of discrete adjustment positions, in each of which the guide member guides the application of the bone preparation tool according to a specific configuration; in some embodiments, the different adjustment positions of the mobile guide features are optionally identified on the plate 11 by distributing them along a trajectory having indicia that graduates according to a logical sequence (e.g., using identification letters, such as the letters "A", "B," and "C" described above, or using a numerical marking—such as that shown in U.S. application Ser. No. 10/793,947—provided that the graphic representations respectively associated on a one-to-one basis with the different adjustment positions include a metric information item corresponding to the numerical markings);

each one of the plurality of graphic representations 20 optionally includes more than one drawing (e.g., drawings from different viewing angles, such as when a plurality of degrees of freedom are to be taken into consideration in positioning the glenoid component 1);

similarly, the series of graphic representations 20 may each include predictive values, resulting from the position of implantation shown on the graphic representation; these values may be, as nonlimiting examples, the articular mobility made possible by the position of implantation shown, the quantification of the articular contact regarding its extent or the stresses transmitted, the quantification of the prosthetic wear, and others; these various mechanical characteristic values linked to the implantation of the glenoid component 1 are notably obtained by virtue of a digital simulation of the virtually prosthesized articulation; and/or rather than having one and the same guide 10 incorporate all the guidance elements respectively associated on a one-to-one basis with the graphic representations 20 available, which may pose bulk problems when these guidance elements are too close to one another, a set of several guides is optionally provided, these guides being provided with respective groups of guide features, each of these groups of guide features being associated on a one-to-one basis with a corresponding group of graphic representations 20; the identifying of the one-to-one link between one of the guides and one of the groups of graphic representations can be provided, for example, using a color marking.

Various additional or alternate modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A surgical system for assisting in the implanting of a glenoid component of a shoulder prosthesis in a patient, the system comprising:
a guide for guiding application of a bone preparation tool to a glenoid, the guide having a bearing face configured to be fitted to the glenoid and guide features for guiding application of the bone preparation tool to the glenoid; and
a series of graphic representations of the glenoid component shown implanted on the glenoid in different implant positions, the respective implant positions of implantation of the glenoid component varying according to a degree of freedom, the guide features being configured to guide the application of the bone preparation tool to the glenoid according to a series of tool positions, each of which is associated with one of the implant positions.

2. The system of claim 1, wherein each graphic representation includes one or more drawings showing the corresponding position of implantation of the glenoid component on the glenoid of the patient.

3. The system of claim 1, wherein each graphic representation includes at least one predictive value representative of a mechanical characteristic associated with the implantation of the glenoid component on the glenoid according to the implant position of the graphic representation.

4. The system of claim 1, wherein the respective implant positions of the glenoid component shown implanted on the glenoid are provided at a plurality of pitches graduating by predetermined values and according to the degree of freedom.

5. The system of claim 1, further comprising a plurality of guides for guiding application of a bone preparation tool to the glenoid, each of the plurality of guides having guide features configured to guide bone preparation tool application to the glenoid according to a series of tool positions, each of which is associated with one of the graphic representations, wherein the graphic representations are visually grouped together into graphic representation groupings, each one of the groupings corresponding to one of the plurality of guides.

6. The system of claim 1, wherein the graphic representations are at least one of on a printed medium and an electronic display.

7. The system of claim 1, wherein the guide features are fixed, each of the fixed guide features being associated on a one-to-one basis with one of the graphic representations.

8. The system of claim 1, wherein the bearing face of the guide is configured to form a customized fit to the glenoid of the patient such that the guide and the glenoid have a predetermined relative position upon assembly of the guide to the glenoid of the patient.

9. The system of claim 1, further comprising complementary indicia on the guide and the series of graphic representations, the complementary indicia being configured to associate each of the tool positions supplied by the guide features with a corresponding one of the plurality of graphic representations.

10. The system of claim 9, wherein the complementary indicia are alphanumeric identifiers.

11. The system of claim 1, wherein the guide includes:
a first portion including the guide features; and
a second portion including the bearing face;
wherein the first portion is movable relative to the second portion to a plurality of pre-selected positions.

12. The system of claim 1, wherein the guide includes:
a first portion including the guide features; and
a second portion including the bearing face;
wherein the first portion is detachably connected to the second portion.

13. The system of claim 1, wherein the guide features are arranged in a grid layout.

14. The system of claim 1, wherein the guide features comprise holes each extending from the bearing face through the guide to a proximal face opposite the bearing face.

15. A surgical system for assisting in the implanting of a glenoid component of a shoulder prosthesis in a patient, the system comprising:
a guide configured to guide a bone preparation tool, the guide having a bearing face configured to be fitted to a glenoid of the patient and guide features each configured to guide the bone preparation tool along a guide axis toward the glenoid, each of the guide axes differing from each other according to a degree of freedom; and
a series of graphic representations of the glenoid component shown implanted on the glenoid in different implant positions, the implant positions of the glenoid component being based on disposing an axis of the glenoid component according to the guide axes.

16. The system of claim 15, wherein the implant positions of the glenoid component are based on aligning the axis of the glenoid component with the guide axes.

17. The system of claim 15, wherein the guide features comprise holes each extending from the bearing face through the guide to a proximal face opposite the bearing face.

18. The system of claim 17, wherein the holes are disposed in a common plane and are inclined relative to one another, and wherein the implant positions of the glenoid component are inclined relative to one another.

19. The system of claim 17, wherein the guide axes of the holes converge at a point on the bearing face.

20. The system of claim 15, further comprising indicia on the guide and the series of graphic representations, the indicia associating each of the guide axes with a corresponding one of the plurality of graphic representations.

21. The system of claim 20, wherein the indicia are alphanumeric identifiers.

\* \* \* \* \*